United States Patent [19]

Ono et al.

[11] Patent Number: 5,032,601

[45] Date of Patent: Jul. 16, 1991

[54] VENOUS EXTENSIBILITY IMPROVING AND CARDIAC HYPERTROPHY SUPPRESSANT AGENT CONTAINING A DIHYDROPYRIDINE COMPOUND

[75] Inventors: Takaharu Ono, Osaka; Minoru Otsuka, Kobe, both of Japan

[73] Assignee: Fujisawa Pharmaceutical Company, Ltd., Osaka, Japan

[21] Appl. No.: 289,665

[22] Filed: Dec. 27, 1988

[30] Foreign Application Priority Data

Dec. 29, 1987 [JP] Japan ................................. 62-335581

[51] Int. Cl.$^5$ ..................... A61K 31/44; C07D 211/78
[52] U.S. Cl. ..................................... 514/344; 546/286
[58] Field of Search ......................... 546/286; 514/344

[56] References Cited

U.S. PATENT DOCUMENTS

| | | | |
|---|---|---|---|
| 4,284,634 | 8/1981 | Sato | 424/266 |
| 4,338,322 | 7/1982 | Sato | 514/344 |
| 4,782,070 | 11/1988 | Ono et al. | 514/344 |

Primary Examiner—Frederick E. Waddell
Attorney, Agent, or Firm—Oblon, Spivak, McClelland, Maier & Neustadt

[57] ABSTRACT

Dihydropyridine compounds of the formula

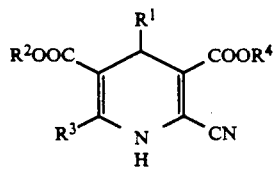

in which $R^1$ is a nitrophenyl group and $R^2$, $R^3$, and $R^4$ are lower alkyl groups or pharmaceutically acceptable salts thereof are useful for improving venous extensibility and suppressing cardiac hypertrophy.

9 Claims, 4 Drawing Sheets

VENOUS EXTENSIBILITY IMPROVING AND CARDIAC HYPERTROPHY SUPPRESSANT AGENT CONTAINING A DIHYDROPYRIDINE COMPOUND

This invention relates to a venous extensibility improving and cardiac hypertrophy suppressant agent. The dihydropyridine compound of the formula:

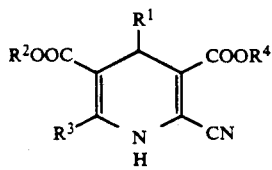

[I]

wherein $R^1$ is a nitrophenyl group and $R^2$, $R^3$ and $R^4$ are each same or different lower alkyl group or a pharmaceutically acceptable salt thereof, which is used in this invention, is a known compound as described in British Patent No. 2,036,722. In regard to its pharmacologic actions, this compound has been found to be of value as an antianginal or antihypertensive agent by virtue of its $Ca^{2+}$ antagonist activity or an antiarteriosclerotic agent and a patent application relevant to the latter agent is now pending in the name of the present applicant (Japanese Patent Unexamined Publication No. 155327/1986).

It is an object of this invention to provide an agent having venous extensibility improving and cardiac hypertrophy suppressant actions.

This invention relates to a venous extensibility improving agent which contains a dihydropyridine compound of formula [I] or a pharmaceutically acceptable salt thereof as an active ingredient.

Referring to formula [I], the nitrophenyl group of $R^1$ includes 2-nitrophenyl, 3-nitrophenyl and 4-nitrophenyl and preferably is 3-nitrophenyl. The lower alkyl group of $R^2$, $R^3$ or $R^4$ is an alkyl group containing 1 to 6 carbon atoms such as methyl, ethyl, propyl, isopropyl, butyl, isobutyl, sec-butyl, pentyl, isopentyl, neopenthyl, 1-methylbutyl, 2-methylbutyl and hexyl, and is preferably an alkyl group containing 1 to 4 carbon atoms. The most desirable example of $R^2$ is isopropyl and the most desirable example of $R^3$ and $R^4$ is methyl.

The pharmaceutically acceptable salt of dihydropyridine compound [I] includes nontoxic salts of the common kinds, for example organic acid addition salts such as acetate, trifluoroacetate, maleate, tartrate, methanesulfonate, benzenesulfonate, formate, toluenesulfonate, etc.; inorganic acid addition salts such as hydrochloride, hydrobromide, hydroiodide, sulfate, nitrate, phosphate, etc.; and acid amino acid salts such as aspartate, glutamate and so on.

While the aforementioned dihydropyridine compound [I] or a pharmaceutically acceptable salt has been shown to be of use as an antianginal agent, antihypertensive agent, or antiarteriosclerotic agent, further research has revealed that the same compound or a salt thereof has venous extensibility improving and cardiac hypertrophy suppressant actions as actions hitherto unknown to its pharmacology.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

Figure 1:
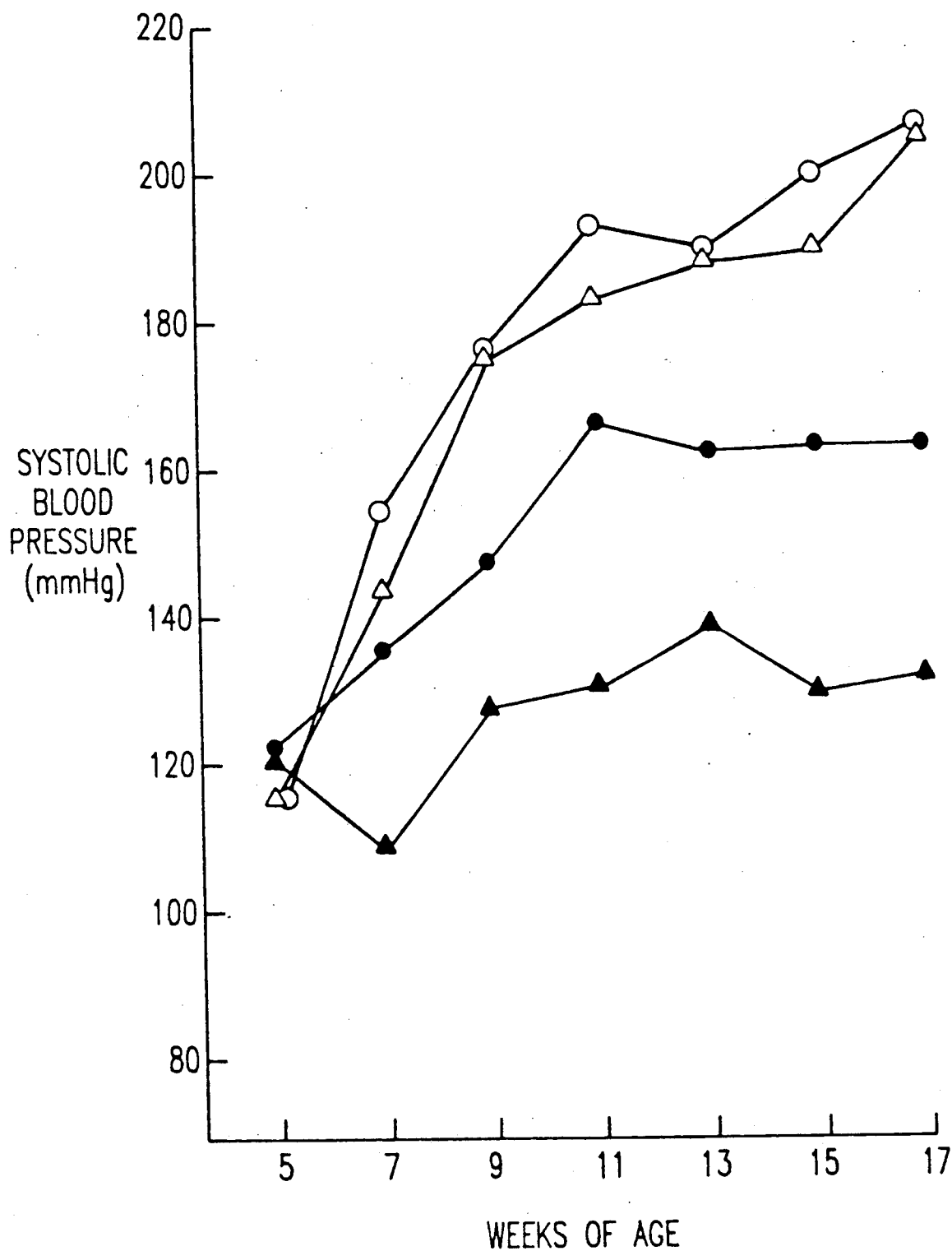
FIG. 1 illustrates the effect of test substances on the onset of hypertension (untreated control, ○; vehicle control, △; dihydropyridine compound A, 1.0 mg/kg, ; dihydropyridine compound A, 3.2 mg/kg, )

It is known that in patients with hypertension as well as in hypertensive animals, cardiac hypertrophy is induced with a comparatively high frequency with the progression of hypertension and it was formerly suspected that an increase in cardiac afterload (resistance on the peripheral side of the heart in the pumping-out of blood) leads to cardiac hypertrophy. However, it has been reported that in the case of hydralazine and minoxidil which are known as vasodilators, clinical or experimental lowering of the elevated blood pressure to the normal level does not necessarily cause an improvement in cardiac hypertrophy [e.g. Sen. S. et al.: Circ. Res., 35 775 (1974); Sen. S. et al.: Cardiovasc. Res., 11 427 (1977)]. Therefore, it has been suggested that factors other than afterload should be taken into consideration.

On the other hand, $Ca^{2+}$ antagonists which are gathering attention as new vasodilators are drugs which inhibit the intracellular uptake of $Ca^{2+}$ and thereby prevent various untoward physiological events associated with such calcium uptake and it is known that these drugs have pharmacological characteristics different from those of the earlier vasodilators and exert excellent hypotensive effects. As drugs belonging to this category, nifedipine and diltiazem are known and it has been reported that these drugs are effective against hypertension-associated cardiac hypertrophy in the high dose range. The dihydropyridine compound [I] according to this invention has also been ranked among $Ca^{2+}$ antagonists but its inhibitory effect on the intracellular uptake of $Ca^{2+}$ is more pronounced than the effects of said nifedipine and diltiazem. Moreover, it is excellent in vascular selectivity and, as a very unique physiological characteristic, has an action to relax the venous smooth muscle contracted by an $\alpha_1$-adrenergic drug, this characteristic being not found in said nifedipine and other drugs classed as $Ca^{2+}$ antagonists. The substances called $Ca^{2+}$ antagonists are varying in chemical structure and have nothing in common and it is considered that even though they may be classed as $Ca^{2+}$ antagocologic actions according to their characteristic chemical structures. Therefore, the present inventors made explorations from a new point of view and discovered that this substance has venous extensibility improving and cardiac hypertrophy suppressant actions. Venous extensibility is an antithesis of venous tension (tonus) and experimentally was determined (1) from the correlation of the change in venous pressure with the volume of a perfusion fluid infused via the rat vena cava and (2) the correlation of the tension generated with the change in cross sectional area of the isolated aorta on stretching. As results of such experiments, dihydropyridine compound [I] was confirmed to produce excellent venous extensibility improving and cardiac hypertrophy suppressant effects. In contrast, it was found that the conventional vasodilator hydralazine has neither a venous extensibility improving effect nor a cardiac hypertrophy suppressant effect and to our still greater surprise, that nicardipine which is also a $Ca^{2+}$ antagonist in the dihydropyridine series fails to show a venous extensibility improving or cardiac hypertrophy suppressant effect. Thus, being a member of the $Ca^{2+}$ antagonist group, dihydropyridine compound [I] of this invention exhibits unique venous extensibility improving and cardiac hypertrophy suppressant actions. Based on these pharmacologic actions, this substance dilates the veins and, hence, reduces the preload on the heart. Then, in consequence, the substance displays clinical efficacy against hypertensive cardiac hypertrophy which does not respond to nicardipine and hydralazine, thus bringing forth clinically meaningful results.

The venous extensibility improving and cardiac hypertrophy suppressant agent of this invention can be administered orally or parenterally to mammalian animals including man in the conventional dosage forms such as capsules, microcapsules, tablets, granules, powders, troches, pills, ointment, suppositories, injection, syrup and so on.

The venous extensibility improving and cardiac hypertrophy suppressant agent of this invention can be manufactured by the established pharmaceutical procedure using organic and/or inorganic carriers or vehicles which are commonly used in the art, for example excipients such as sucrose, starch, mannitol, sorbitol, lactose, glucose, cellulose, talc, calcium phosphate, calcium carbonate, etc.; binders such as cellulose, methylcellulose, hydroxymethylcellulose, polypropylpyrrolidone, gelatin, gum arabic, polyethylene glycol, sucrose, starch, etc.; disintegrating agents such as starch, carboxymethylcellulose, hydroxypropylstarch, sodium hydrogen carbonate, calcium phosphate, calcium citrate, etc.; lubricating agents such as magnesium stearate, aerosil, talc, sodium laurylsulfate, etc.; corrigents such as citric acid, menthol, glycine, orange powder, etc.; preservatives such as sodium benzoate, sodium bisulfite, methylparaben, propylparaben, etc. stabilizers such as citric acid, sodium citrate, acetic acid, etc.; suspending agents such as methylcellulose, polyvinylpyrrolidone, aluminum stearate, etc.; dispersing agents such as hydroxypropylmethylcellulose etc.; diluents such as water etc.; ointment bases such as cacao butter, white petrolatum, polyethylene glycol, etc., and so on.

The dosage of dihydropyridine compound [I] dependes on the patient's body weight and/or age, the severity of disease and/or various other factors such as the method of administration. Usually, however, 0.5 to 1000 mg, and preferably 1 to 500 mg, per day is administered by the oral route. The effective dose per kilogram body weight is selected from the range of 0.01 to 20 mg and preferably 0.05 to 2 mg.

To substantiate the usefulness of the dihydropyridine compound [I] or pharmaceutically acceptable salt which is used as an active ingredient of the venous extensibility improving and cardiac hypertrophy suppressant agent of this invention, pharmacological data on the compound are presented below.

TEST COMPOUND

Isopropyl 6-cyano-5-methoxycarbonyl-2-methyl-4-(3-nitrophenyl)-1,4-dihydropyridine-3-carboxylate (hereinafter referred to as dihydropyridine compound A).

METHOD (1) Animals

Spontaneously hypertensive rats (SHR), male and 4 weeks of age, were divided into the following 6 groups: untreated control, vehicle control, dihydropyridine A 1.0 and 3.2 mg/kg, hydralazine 3.2 mg/kg and nicardipine 3.2 mg/kg.

(2) Administration

The substance was administered to SHRs for 12 weeks beginning at 5 weeks of age. The administration was invariably carried out by the subcutaneous route at the frequency of once a day (except on Saturdays and Sundays). The vehicle control group received a mixture of polyethylene glycol (PEG), ethanol (EtOH) and distilled water. This mixture was of the same composition as the vehicle in which the test substance and reference substances were dissolved.

(3) Measurement of blood pressure

Before the beginning of administration (at 5 weeks of age) and every 2 weeks after the beginning of administration, the systolic blood pressure was measured at the tail artery. This measurement was carried out at 24 hours after each administration. The SHRs were put in an environment controlled at about 40° C. at 10 minutes preceding the blood pressure measurement.

(4) Determination of venous extensibility

The SHRs which had gone through the 12-week repeated administration period were used. Each animal was anesthetized with i.p. administration of 40 mg/kg of pentobarbital sodium and a catheter was inserted into the left femoral vein. Then, laparotomy was performed and the portion of the intestinal tract inclusive of the duodenum through the sigmoid colon was excised. Thereafter, an arterial perfusion catheter was inserted into the aorta immediately below the renal artery and a drainagevenous perfusion catheter into the inferior vena cava, each towards the hindlimb, and the abdominal region inclusive of the spinal cord and surrounding muscles and skin was tightly ligated immediately below the renal artery to interrupt the longitudinal vascular communication.

After the catherter inserted into the left femoral vein was connected to a pressure transducer, 1000 U/kg of heparin sodium was intravenously administered. Then, with the inferior vena cava being kept open, oxygenated $(95\%O_2+5\%CO_2)$ krebs-Henseleit solution (37° C.) containing 7% of dextran was infused from the aortic catheter at a constant rate to replace all the arterial and venous blood with the nutrient solution. Thereafter, the arterial perfusion was suspended and drainage from the inferior vena cava was performed for a few minutes to lower the femoral venous pressure to 0-5 mmHg. Then, the nutrient solution was retrogradely infused from the inferior vena cava at a rate of 15 ml/minute and the resulting change in femoral venous pressure was recorded on a thermal pen-writing recorder. From the volume of infusion and the change in venous pressure, the hindlimb venous pressure-volume curve was constructed to evaluate the venous extensibility.

(5) Determination of extensibility (tonus) of the isolated inferior vena cava

After completion of the above determination of venous extensibility, the inferior vena cava was excised from each SHR and suspended in a Magnus tube containing oxygenated Krebs-Henseleit solution at 37° C. After the venous strip was connected to a tension transducer, a tension of 50 mg was applied in the direction of longitudinal muscle and the length of the strip was measured 5 minutes after loading. Then, the venous strip was stretched to 150% of its initial length and the resulting tension was measured via an ink writing recorder. After this determination, the vena cava was weighed and the cross sectional area (C) of the specimen was calculated by means of the following equation. The stress (tonus) value was also calculated as generated tension (T) divided by cross sectional area.

$$C (cm^2) = weight (g)/[1.05* \times length (cm)]$$

*: specific gravity of the specimen $$Stress (g/cm^2) = T (g)/C (cm^2)$$

(6) Weighing of the left ventricle, and blood biochemistry

Immediately before the above determination of venous extensibility, the blood was drawn from the abdominal aorta and centrifuged at 4° C. and 3,000 rpm for 10 minutes to separate the plasma. Using Technicon's SMAC, biochemical testing of the plasma was carried out.

After the determination of venous extensibility, the animal was bled to death and the heart was excised. From the isolated heart, the blood was removed with filter paper and the bilateral atrial muscles and further, the right ventricular free wall were excised. Then, the left ventricle was weighed.

(7) Statistical analysis

The results were invariably expressed in mean ±S.E. The 5% level of significance was used.

RESULTS (1) Effect on the onset of hypertension

As shown in FIG. 1, in the untreated control and vehicle control groups, the systolic blood pressure was in the neighborhood of 120 mmHg before the beginning of administration (at 5 weeks of age) but rose to about 190 mmHg after 6 weeks of treatment (at 11 weeks of age). Thereafter, the blood pressure rose at a somewhat attenuated pace and registered about 210 mmHg at 12 weeks of treatment (at 17 weeks of age).

In the dihydropyridine compound A 1.0 and 3.2 mg/kg groups, the elevation of systolic blood pressure was significantly and dose-dependently inhibited from 2-4 weeks after the beginning of administration and the levels in these groups were lower than the vehicle control level by about 20–40 mmHg and 50–60 mmHg, respectively. In the dihydropyridine compound A 3.2 mg/kg group, the systolic blood pressure never exceeded 140 mmHg throughout the administration period but was controlled substantially at the normal level.

Figure 2:
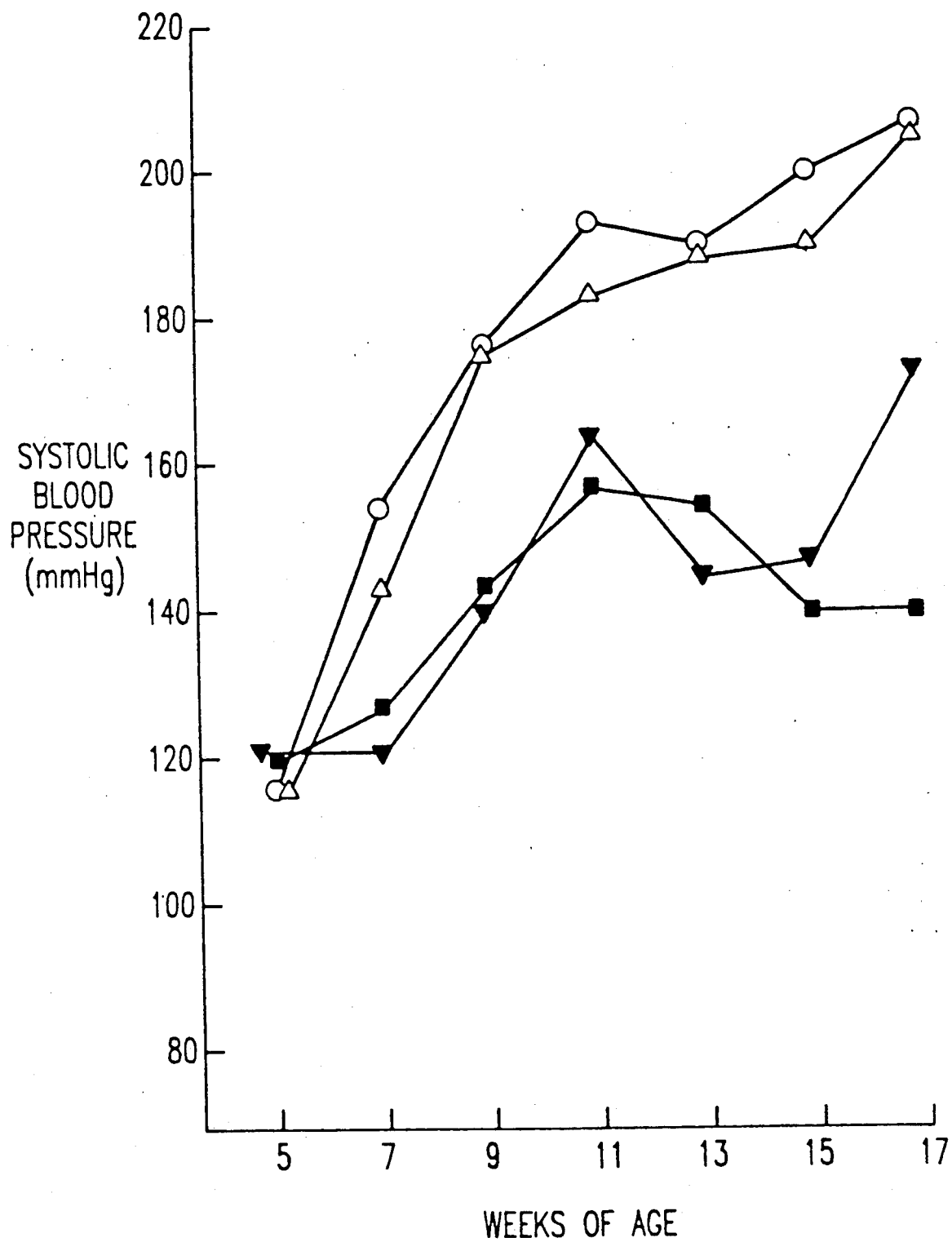
FIG. 2 illustrates the effect of test substances on the onset of hypertension (untreated control, ○; vehicle control, △; hydrazaline, 3.2 mg/kg, ; nicardipine, 3.2 mg/kg, )

In the hydralazine (3.2 mg/kg) and nicardipine (3.2 mg/kg) groups, too, a significant inhibition of systolic blood pressure increase began to be recognized 2 weeks after the beginning of administration and the effects of the two drugs were almost comparable (FIG. 2). Moreover, the hypotensive effects of these two drugs were roughly intermediate between the effect of dihydropyridine compound A 1.0 mg/kg and that of dihydropyridine compound A 3.2 mg/kg.

The time courses of body weight of animals in the drug treatment groups were almost comparable to those of animals in the vehicle control and untreated control groups.

(2) Effect on venous extensibility (a) Hindlimb venous pressure-volume curve

Figure 3:
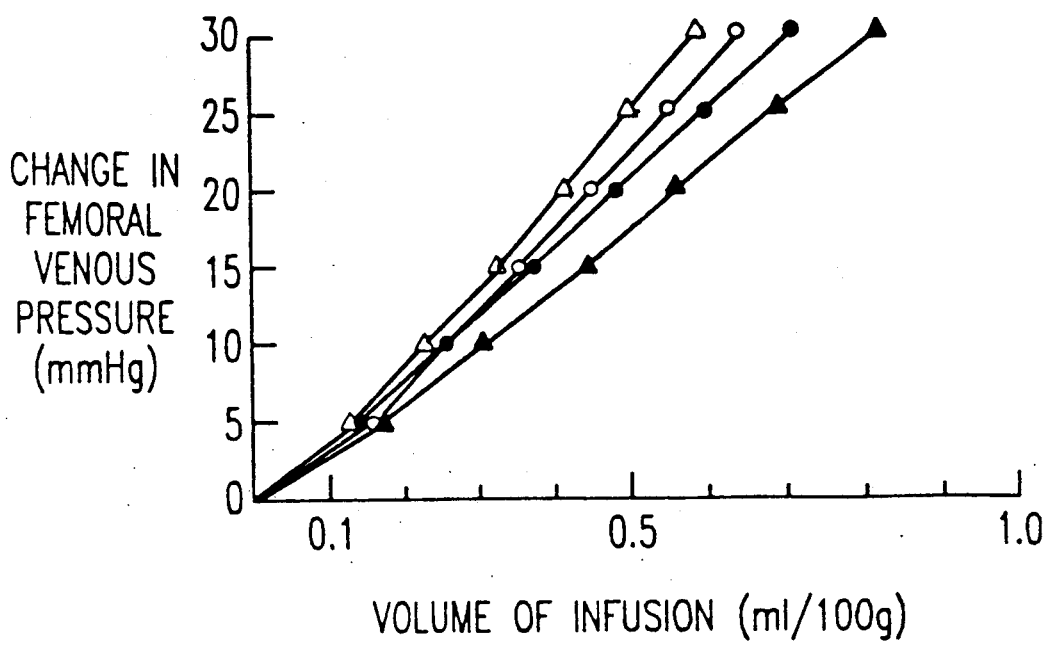
FIG. 3 illustrates the effect of test substances on hindlimb venous pressure-volume curves (vehicle control, n=8, △; untreated control, n=7, ○; dihydropyridine compound A, 1.0 mg/kg, n=14, ; dihydropyridine, compound A, 3.2 mg/kg, n=17, )
Figure 4:
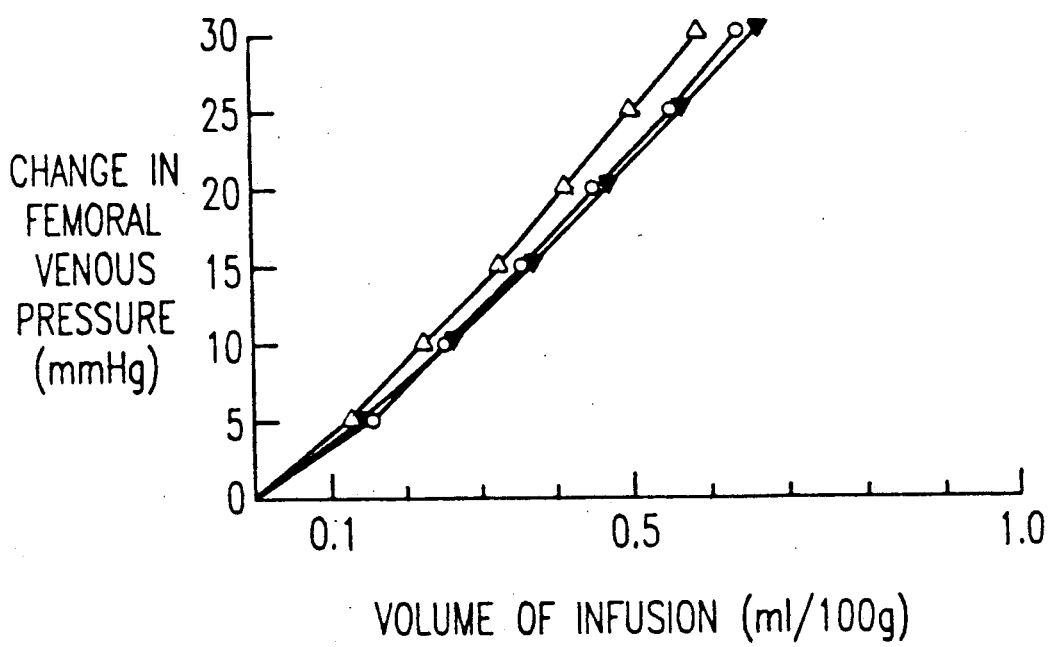
FIG. 4 illustrates the effect of test substances on hindlimb venous pressure-volume curves (vehicle control, n=8, △; untreated control, n=7, ○; hydralazine, 3.2 mg/kg, n=8, )
Figure 5:
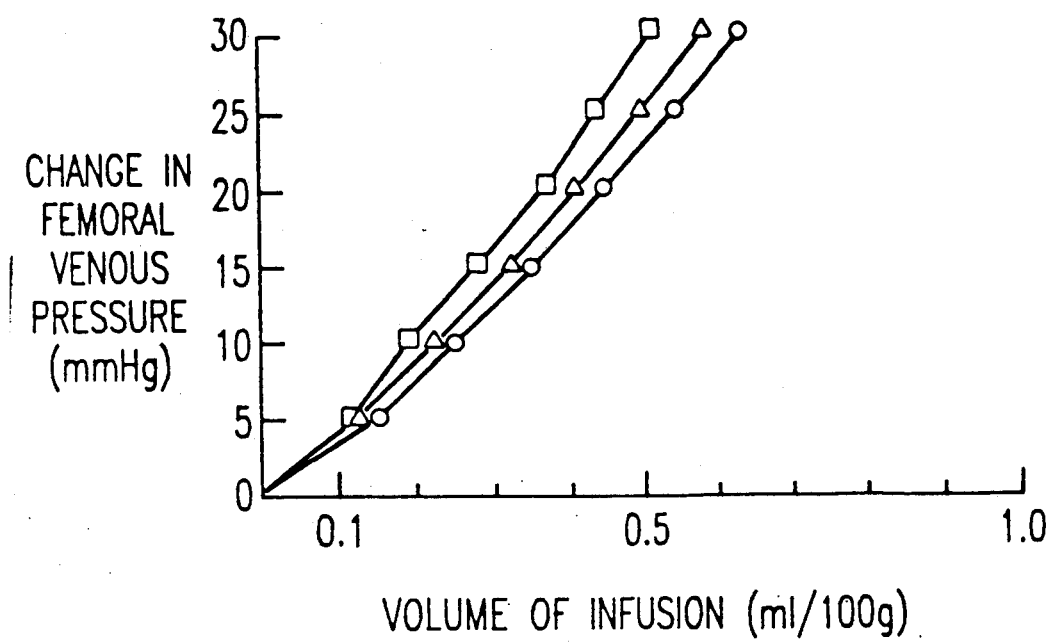
FIG. 5 illustrates the effect of test substances on hindlimb venous pressure-volume curves (vehicle control, n=8, △; untreated control, n=7, ○; nicardipine, 3.2 mg/kg, n=9, □)

FIGS. 3 to 5 show hindlimb venous pressure-volume curves. The hindlimb venous pressure-volume curves of the dihydropyridine compound A 1.0 and 3.2 mg/kg groups were both significantly shifted towards the higher end of the volume scale from the curve of the vehicle control group and the magnitude of this shift was greater with an increasing dosage of dihydropyridine compound A (FIG. 3).

On the other hand, neither the hindlimb venous pressure-volume curve of the hydralazine group (FIG. 4) nor that of the nicardipine group (FIG. 5) showed a significant difference from the curves of the vehicle control and untreated control groups.

(b) Isolated inferior vena cava

Figure 6:
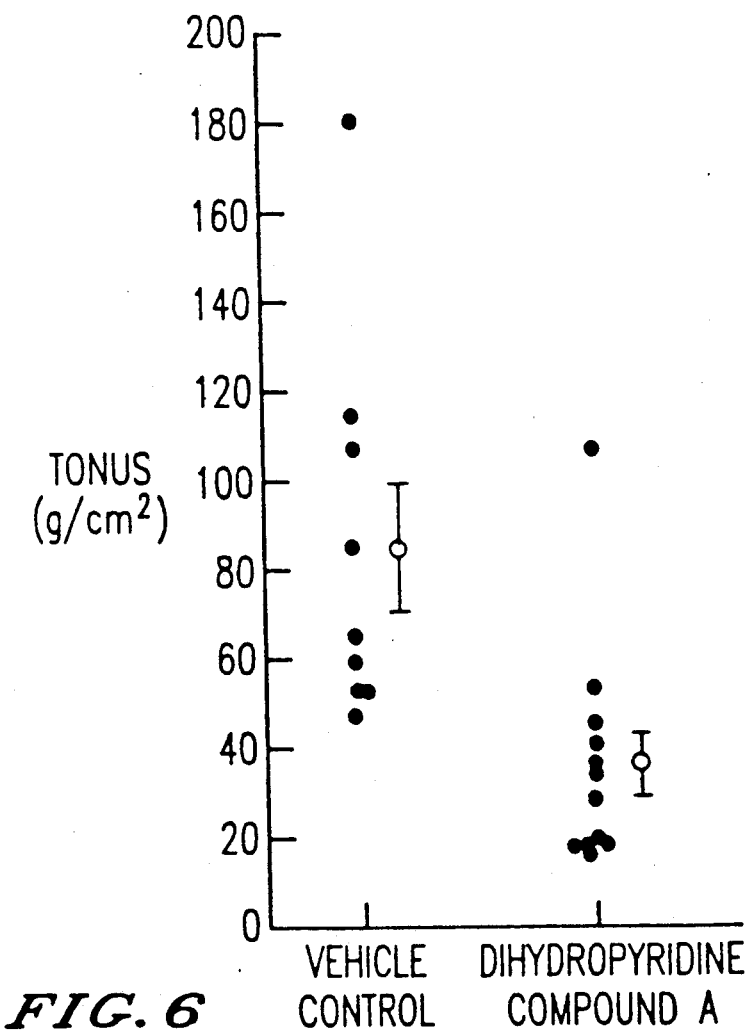
FIG. 6 illustrates the tension stress generated upon stretching of the isolated inferior vena cava for the vehicle control group and the dihydropyridine compound A (3.2 mg/kg) group.

FIG. 6 shows the values of stress generated on stretching of the inferior vena cava specimens in the dihydropyridine compound A groups. Compared with the mean stress value of $84.9 \pm 14.3$ g/cm$^2$ in the vehicle control group, the value of $36.5 \pm 7.2$ g/cm$^2$ in the dihydropyridine compound A 3.2 mg/kg group was significantly lower.

(3) Effect on left ventricular weight

Table 1 shows the left ventricular weights in the respective groups. Whereas the left ventricular weight in the vehicle control group was $306 \pm 3$ mg per 100 g body weight, the left ventricular weights in the dihydropyridine compound A 1.0 mg/kg and 3.2 mg/kg groups were $278 \pm 3$ mg and $264 \pm 2$ mg, respectively, showing significantly lower values in a dose-related manner. The values in the hydralazine and nicardipine groups were $306 \pm 8$ mg and $311 \pm 6$ mg, respectively Neither of these values was significantly different from the values in the vehicle control and untreated control groups.

TABLE 1

| Group | | n | Left ventricular weight (mg/100 g body weight) |
|---|---|---|---|
| Vehicle* | | 9 | 306 ± 3 |
| Untreated | | 10 | 315 ± 4 |
| Dihydropyridine | 1 mg/kg | 14 | 278** ± 3 |
| compound A | 3.2 mg/kg | 17 | 264** ± 2 |
| Hydralazine | 3.2 mg/kg | 10 | 306 ± 8 |
| Nicardipine | 3.2 mg/kg | 10 | 311 ± 6 |

*PEG-EtOH-distilled water = 1:1:2 (0.1 ml/100 g)
**p<0.01, compared with vehicle control group

EXAMPLES

EXAMPLE 1

Dihydropyridine compound A: 100 g
Hydroxypropylmethylcellulose: 500 g

Dihydropyridine compound A was dissolved in absolute ethanol (5 l), followed by addition of hydroxypropylmethylcellulose to give a suspension. The organic solvent was then removed under reduced pressure to provide a solid dispersion.

EXAMPLE 2

Dihydropyridine compound A: 100 g
Hydroxypropylmethylcellulose: 500 g
Sucrose: 9.4 kg Sucrose was added to a suspension of dihydropyridine compound A and hydroxypropylmethylcellulose in absolute ethanol (5 l) and the resulting mixture was stirred. The organic solvent was then removed under reduced pressure to give a solid dispersion. This composition was processed into fine granules in the routine manner.

EXAMPLE 3

Dihydropyridine compound A: 100 g
Hydroxypropylmethylcellulose: 500 g
Lactose: 6.87 kg
Hydroxypropylcellulose with a low degree of substitution: 1.5 kg
Magnesium stearate: 30 g Lactose and hydroxypropylcellulose with a low degree of substitution were added to a suspension of dihydropyridine compound A and hydroxypropylmethylcellulose in absolute ethanol (5 l) and the resulting mixture was stirred. The organic solvent was then removed under reduced pressure to give a solid dispersion. This composition was granulated by the routine procedure and with the addition of magnesium stearate, the granulation was processed into tablets in the routine manner. Each of these tablets contains 2 mg of dihydropyridine compound A.

EXAMPLE 4

The tablets prepared in Example 3 were film-coated using a coating composition of hydroxypropylmethylcellulose (5.1 mg), titanium dioxide (1.6 mg), polyethylene glycol 6000 (0.8 mg), talc (0.4 mg) and yellow iron oxide (0.1 mg) in the routine manner. The procedure gives film-coated tablets each containing 2 mg of dihydropyridine compound A.

What is claimed is:

1. A method for improving venous extensibility and suppressing cardiac hypertrophy, which comprises administering a dihydropyridine compound of the formula:

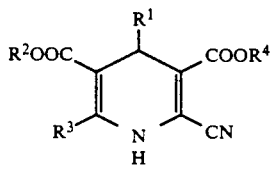

wherein $R^1$ is a nitrophenyl group and $R^2$, $R^3$ and $R^4$ are each the same or different lower alkyl group or a pharmaceutically acceptable salt thereof to a mammal suffering from cardiac hypertrophy.

2. The method of claim 1, wherein said dihydropyridine compound is isopropyl 6-cyano-5-methoxycarbonyl-2-methyl-4-(3-nitrophenyl)-1,4-dihydropyridine-3-carboxylate.

3. The method of claim 1, wherein $R^2$ is isopropyl.

4. The method of claim 1, wherein $R^3$ and $R^4$ are each methyl.

5. The method of claim 1, wherein said compound or pharmaceutically acceptable salt thereof is administered in an amount of 0.5 to 1,000 mg per day.

6. The method of claim 5, wherein said compound or pharmaceutically acceptable salt thereof is administered in an amount of 1 to 500 mg per day.

7. The method of claim 1, wherein said compound or pharmaceutically acceptable salt thereof is administered in an amount of 0.01 to 20 mg per kilogram of body weight.

8. The method of claim 7, wherein said compound or pharmaceutically acceptable salt thereof is administered in an amount of 0.05 to 2 mg per kilogram of body weight.

9. The method of claim 1, wherein said mammal is a human being.